(12) United States Patent
Watanabe et al.

(10) Patent No.: US 9,638,923 B2
(45) Date of Patent: May 2, 2017

(54) OPTICAL ELEMENT FOR TERAHERTZ WAVES

(75) Inventors: Makoto Watanabe, Tsukuba (JP);
Dmitry Bulgarevich, Tsukuba (JP);
Mitsuharu Shiwa, Tsukuba (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 37 days.

(21) Appl. No.: 14/131,759

(22) PCT Filed: Jul. 5, 2012

(86) PCT No.: PCT/JP2012/067189
§ 371 (c)(1),
(2), (4) Date: Apr. 21, 2014

(87) PCT Pub. No.: WO2013/008713
PCT Pub. Date: Jan. 17, 2013

(65) Prior Publication Data
US 2014/0300955 A1    Oct. 9, 2014

(30) Foreign Application Priority Data

Jul. 13, 2011  (JP) .................................. 2011-154432

(51) Int. Cl.
*G02B 27/09*       (2006.01)
*G02B 5/00*        (2006.01)
(Continued)

(52) U.S. Cl.
CPC ..... *G02B 27/0988* (2013.01); *G01N 21/3581* (2013.01); *G01N 21/3586* (2013.01);
(Continued)

(58) Field of Classification Search
None
See application file for complete search history.

(56) References Cited

U.S. PATENT DOCUMENTS

| 6,649,901 B2 | 11/2003 | Thio et al. |
| 2005/0161589 A1* | 7/2005 | Kim ...................... B82Y 20/00 |
| | | 250/216 |

(Continued)

FOREIGN PATENT DOCUMENTS

| JP | A2009026360 | 2/2009 |
| JP | A-2011-014857 | 1/2011 |
| JP | A2011253142 | 12/2011 |

OTHER PUBLICATIONS

K. Ishihara, K. Ohashi, T. Ikari, H. Minamide, H. Yokoyama, J. Shikata, H. Ito, "Terahertz-wave near-field imaging with subwavelength resolution using surface-wave-assisted bow-tie aperture", Applied Physics Letters 89 (2006) 201120.

(Continued)

*Primary Examiner* — Stephone B Allen
*Assistant Examiner* — James McGee
(74) *Attorney, Agent, or Firm* — Hoffmann & Baron, LLP (57) ABSTRACT

An optical element for terahertz waves that transmits terahertz-wave incident beams through itself after being compressed into half or less a wavelength of the beam, the optical element comprising: a substrate that allows terahertz waves to be transmitted through itself; and a conductive coat that covers a surface of the substrate and is capable of blocking the waves, wherein the coat has an aperture provided in a circular region and ring-shaped grooves, provided on a surface of the coat, having the same center as the circular region and having radii which increase every fixed length, and wherein in the circular region, four or more fan-shaped tips each having an arc with the same radius of curvature as the radius of the region, are arranged at equal distances toward the center of the circle without contacting each other as the arc contacts an outer periphery of the region.

8 Claims, 12 Drawing Sheets

(51) Int. Cl.
G02B 6/122 (2006.01)
G02B 27/58 (2006.01)
G01N 21/3581 (2014.01)
G01N 21/3586 (2014.01)

(52) U.S. Cl.
CPC ............ *G02B 5/008* (2013.01); *G02B 6/1226* (2013.01); *G02B 27/58* (2013.01)

(56) References Cited

U.S. PATENT DOCUMENTS

| | | | |
|---|---|---|---|
| 2007/0262405 A1 | 11/2007 | Furuyama | |
| 2008/0174509 A1* | 7/2008 | Williams | F41G 7/2246 343/872 |
| 2008/0185521 A1* | 8/2008 | Hollingsworth | B82Y 20/00 250/338.1 |

OTHER PUBLICATIONS

T. Thio, H.J. Lezec, T.W. Ebbesen, K.M. Pellerin, G.D. Lewen, A. Nahata, R.A. Linke, "Giant optical transmission of sub-wavelength apertures: physics and applications", Nanotechnology 13 (2002) 429-432.
B.S. Dmitry, M. Watanage, M. Shiwa, "Highly-efficient aperture array terahertz band-pass filtering", Optics Express, 18 (2010) 25250-25255.
Bethe, H.A., "Theory of diffraction by small holes", Physical Review, 66 (1944) 163-182.
M.J. Lockyear, A.P. Hibbins, J.R. Sambles, C.R. Lawrence, "Surface-topography-induced enhanced transmission and directivity of microwave radiation through a subwavelength circular metal aperture", Applied Physics Letters, 84 (2004) 2040-2042.
G.A. Valaskovic, M. Holton, G.H. Morrison, "Parameter control, characterization, and optimization in the fabrication of optical fiber near-field probes", 1995 Applied Optics, 34 (1995) 1215-1218.
D S Bulgarevich, et al., "Single sub-wavelength aperture with greatly enhanced transmission", New Journal of Physics, 14 2012.
International Search Report for PCT/JP2012/067189.
Dmitry S. Bulgarevich et al., "Highly efficient aperture array terahertz band-pass filters", Infrared Millimeter and Terahertz Waves (IRMMW-THZ), 2010 35th International Conference on, IEEE, Piscataway, NJ, USA, Sep. 5, 2010 (Sep. 5, 2010), pp. 1-2.
EPO Search Report issued in corresponding EPO Patent Application No. 12810782.8 dated Feb. 16, 2015.
Japanese Office Action issued in corresponding Japanese Patent Application No. 2013-523915.

* cited by examiner

OPTICAL ELEMENT FOR TERAHERTZ WAVES

TECHNICAL FIELD

The present invention relates to an optical element having a fine aperture through which terahertz waves incident on one surface side are emitted from the other surface side with a high transmittance. More specifically, the present invention relates to an optical element that allows terahertz waves to be transmitted therethrough with a high transmittance, without increasing the aperture diameter, due to having a special aperture shape.

Priority is claimed on Japanese Patent Application No, 2011-154432, filed Jul. 13, 2011, the content of which is incorporated herein by reference.

BACKGROUND ART

In the present invention, the terahertz wave means an electromagnetic wave with a frequency in a region of 0.1 to 10 THz (1 THz=$10^{12}$ Hz), accordingly, a wavelength of 0.03 to 3 mm.

Terahertz wave are expected to be applied to a wide variety of fields, such as security, information and communications, medical treatment, non-destructive inspection, molecular structure analysis, and radio astronomy. Since the terahertz wave can be transmitted through a material through which visible light cannot pass, it is possible to detect a material-specific spectrum depending on the material. For this reason, it is expected that imaging techniques or spectroscopic techniques using a terahertz wave can be very useful techniques in the field of a biopsy for a human body and the like or in the field of material inspection, such as identification of chemical substances or damage detection.

However, the wavelength of the terahertz wave is 0.03 to 3 mm, which is very long compared with the wavelength of 0.00036 to 0.00083 mm (=360 to 830 nm) of visible light. Since the spatial resolution in imaging using electromagnetic waves is limited to half the wavelength due to the diffraction limit, there is a problem in that the resolution is low compared with an image based on visible light or the like.

On the other hand, an element has been developed in which an electromagnetic wave is emitted and transmitted through a fine aperture, which is less than or equal to the wavelength of the electromagnetic wave, to obtain a fine beam spot having the same size as the aperture (refer to PTL 1 and NPL 1). By using this element, a spatial resolution comparable to the size of the beam spot can be realized. Accordingly, this element is very useful for high-resolution imaging or high-resolution spectroscopy.

However, as the size of the aperture is decreased in order to obtain a finer beam spot, the transmittance of the electromagnetic wave is dramatically reduced in inverse proportion to the fourth power of the radius of the aperture. For this reason, in order to take advantage of the finer beam spot, it becomes an issue to increase the transmittance.

PTL 2 and NPL 2 disclose an optical element in which a circular aperture is provided in the center of a metal plate and a plurality of ring-shaped grooves, which have the same center as the circular aperture and whose radii are different by a fixed length, are formed around the aperture, and have reported that the transmittance of light is increased compared with a case where there is no ring-shaped groove. Their study provides important information that the central aperture is a circle but the transmittance is increased by forming a plurality of ring grooves. When $d/\lambda$, which is the ratio of the central circular hole diameter d and the wavelength $\lambda$ of the incident electromagnetic wave, is 0.25, the transmittance of 0.001 (=0.1%) is achieved.

In addition, NPL 1 discloses that the transmittance is increased by making the aperture shape of a central portion as a bow-tie shape instead of a circular shape and performing ring-shaped groove machining around the aperture, and clearly shows that the aperture shape of the central portion has a large influence on the transmittance. The transmittance is improved 5 times compared with a case where the aperture shape of the central portion is a mere circular aperture.

The inventors invented an array terahertz-wave filter, in which a number of fine apertures having a special shape are periodically placed at fixed distances, so far (refer to NPL 3). With this terahertz-wave filter, the inventors have succeeded in selectively intensifying only a specific frequency component and making the specific frequency component transmitted through the terahertz-wave filter depending on the shape of the aperture and the periodicity of the aperture arrangement.

CITATION LIST

Patent Literature

[PTL 1] Japanese Unexamined Patent Application, First Publication No. 2009-26360
[PTL 2] U.S. Pat. No. 6,649,901

Non-Patent Literature

[NPL 1] K. Ishihara, K. Ohashi, T. Ikari, H. Minamide, H. Yokoyama, J. Shikata, H. Ito, "Terahertz-wave near-field imaging with subwavelength resolution using surface-wave-assisted bow-tie aperture", Applied Physics Letters 89 (2006) 201120.
[NPL 2] T, Thio, H. J. Lezec, T. W Ebbesen, K. M. Pellerin, G D. Lewen, A. Nahata, R. A. Linke, "Giant optical transmission of sub-wavelength apertures: physics and applications", Nanotechnology 13 (2002) 429-432.
[NPL 3] B. S. Dmitry, M. Watanabe, M. Shiwa, "Highly-efficient aperture array terahertz band-pass filtering", Optics Express, 18 (2010) 25250-25255.
[NPL 4] Bethe, H. A., "Theory of diffraction by small holes", Physical Review, 66 (1944) 163-182.
[NPL 5] M. J. Lockyear, A. P. Hibbins, J. R. Sambles, C. R. Lawrence, "Surface-topography-induced enhanced transmission and directivity of microwave radiation through a subwavelength circular metal aperture", Applied Physics Letters, 84 (2004) 2040-2042.
[NPL 6]G. A. Valaskovic, M. Holton, G. H. Morrison, "Parameter control, characterization, and optimization in the fabrication of optical fiber near-field probes" 1995 Applied Optics, 34 (1995) 1215-1218,

SUMMARY OF INVENTION

Technical Problem

In the conventional element described above, the transmittance, which is the ratio of the intensity of the incident electromagnetic wave and the intensity of the transmitted electromagnetic wave, is less than 1%. For this reason, there is a problem in that transmitted electromagnetic waves cannot be detected due to negligible electrical noise or mechanical noise. The terahertz wave becomes an extremely weak electromagnetic wave after being transmitted through the optical element. Furthermore, when making the terahertz wave incident on an object to be observed and transmitted therethrough, it becomes more difficult to detect the transmitted electromagnetic wave due to the attenuation in the object. Since the attenuation in the object depends on the type or the thickness of the object, there is a problem in that an observable material or the size is limited.

The present invention has been made to solve the problem described above. That is, it is an object of the present invention to provide a optical element for terahertz waves that uses a fine aperture having a size less than or equal to half the wavelength of a terahertz wave and that has a high transmittance of 2.5% or more compared with the transmittance of a conventional element, which is less than 1%.

Solution to Problem

A first aspect of this invention is an optical element for terahertz waves that transmits terahertz-wave incident beams through itself after being compressed into half or less a wavelength of the terahertz-wave incident beam. The optical element includes a substrate that allows terahertz waves to be transmitted through itself; and a conductive coat that covers a single surface of the substrate and is capable of blocking the terahertz waves. The coat has an aperture provided in a circular region and a plurality of ring-shaped grooves, which are provided on a surface of the coat and have the same center as the circular region and whose radii increase every fixed length. In the circular region, four or more fan-shaped tips each of which has an arc with the same radius of curvature as the radius of the circular region, are arranged at equal distances toward the center of the circle without being in contact with each other in a state where the arc is in contact with an outer periphery of the circular region.

In the optical element for terahertz waves according to the first aspect, a portion, which is not covered by the fan-shaped tips, in the circular region forms the aperture. It is preferable that the fan-shaped tip be formed of a conductive material capable of blocking terahertz waves. This material may be the same as a material that forms the coat. The coat and the tips may be integrally formed.

A second aspect of the invention is the optical element characterized in that the substrate is formed of any material selected from the group consisting of silicon, crystal, sapphire, polyethylene, polypropylene, TEFLON® (polytetrafluoroethylene (PTFE) based formulas), and polymethyl menthene which are terahertz wave transmissive resins, and terahertz wave transmissive glass.

A third aspect of the present invention is the optical element according to the first or second aspect in which the coat is formed of any metal of Al, Au, Cu, Ag, Pt, Cr, and Ni or an alloy of the metals.

A fourth aspect of the present invention is the optical element according to any one of the first to third aspects in which, assuming that the radius of the circular region is $R_a$, 0.003 mm $\leq R_a \leq$ 0.3 mm.

A fifth aspect of the present invention is the optical element according to any one of the first to fourth aspects in which the number of tips present in the circular region is 4 to 320.

A sixth aspect of the present invention is the optical element according to any one of the first to fifth aspects in which, assuming that an tip flare angle of a tip apex of each tip is $\alpha$, $1.15° \leq \alpha \leq 40°$.

A seventh aspect of the present invention is the optical element according to any one of the first to sixth aspects in which a shortest distance between tip apexes of the tips is 0.1 to 10 µm.

An eighth aspect of the present invention is the optical element according to any one of the first to seventh aspects in which the circular region is located in the center of the coat.

Advantageous Effects of invention

According to the optical element based on the special design of the present invention, for example, even if the diameter of the aperture region is set to be small (for example, 50 µm), the optical element has a very high transmittance (for example, a few percent) for the terahertz wave. Therefore, the development of a high-resolution terahertz microscope or the use as a high-sensitivity chemical sensor can be expected. In addition, by using a rigid substrate, such as silicon, as the substrate, it is possible to provide an optical element that is extremely rigid and can be handled more easily compared with a conventional optical element in which only a metal film is processed.

DESCRIPTION OF EMBODIMENTS

Hereinafter, embodiments of the present invention will be described referring to the drawings.

Figure 1:
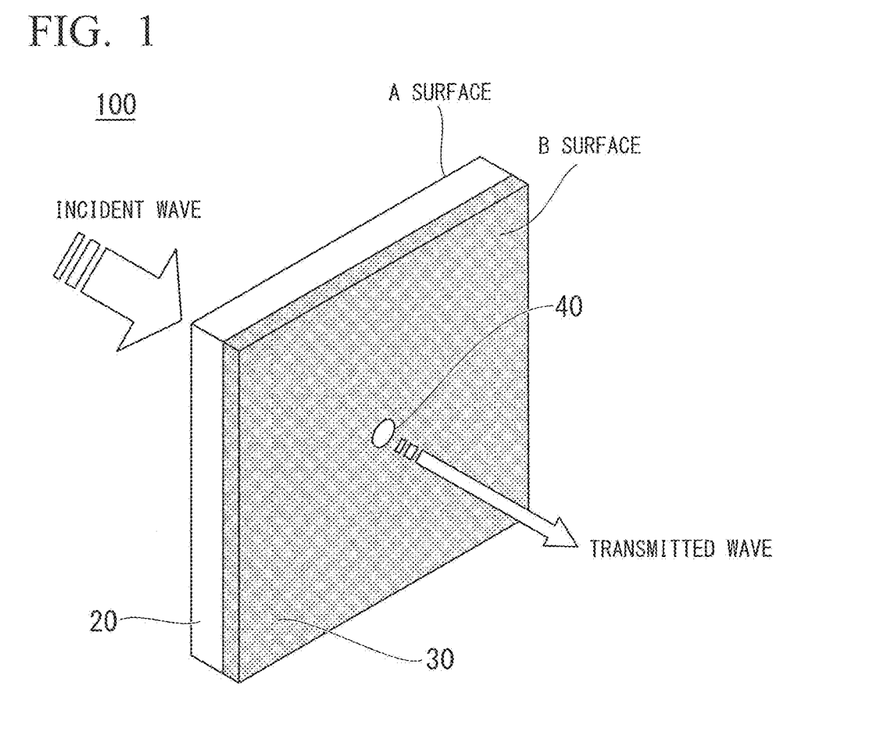
FIG. 1 is a diagram showing the appearance of an entire optical element for terahertz waves., which is an embodiment of the present invention, and the arrangement for an incident wave. The incident wave is incident from the A surface on the substrate side and is emitted from the B surface side of a mask surface.

FIG. 1 is a perspective view showing an optical element according to an embodiment of the present invention. As shown in FIG. 1, an optical element 100 of the present embodiment has a plate shape formed of two kinds of materials, and a mask (coat) 30 formed of a conductive material (material 2) is formed on a plate-shaped substrate 20 formed of a predetermined material (material 1). The material of the substrate 20 allows terahertz waves to be transmitted therethrough, and the material of the mask blocks terahertz waves. An aperture 40 through which a part of the substrate 20 is exposed is provided in the mask 30, and the aperture 40 is formed in a circular region (aperture region). A plurality of ring-shaped grooves is provided around the aperture 40 concentrically with the circular aperture region. The optical element 100 emits terahertz waves, which are incident from the surface (A surface) side of the substrate, toward the surface (B surface) side of the mask with a high transmittance.

Figure 2:
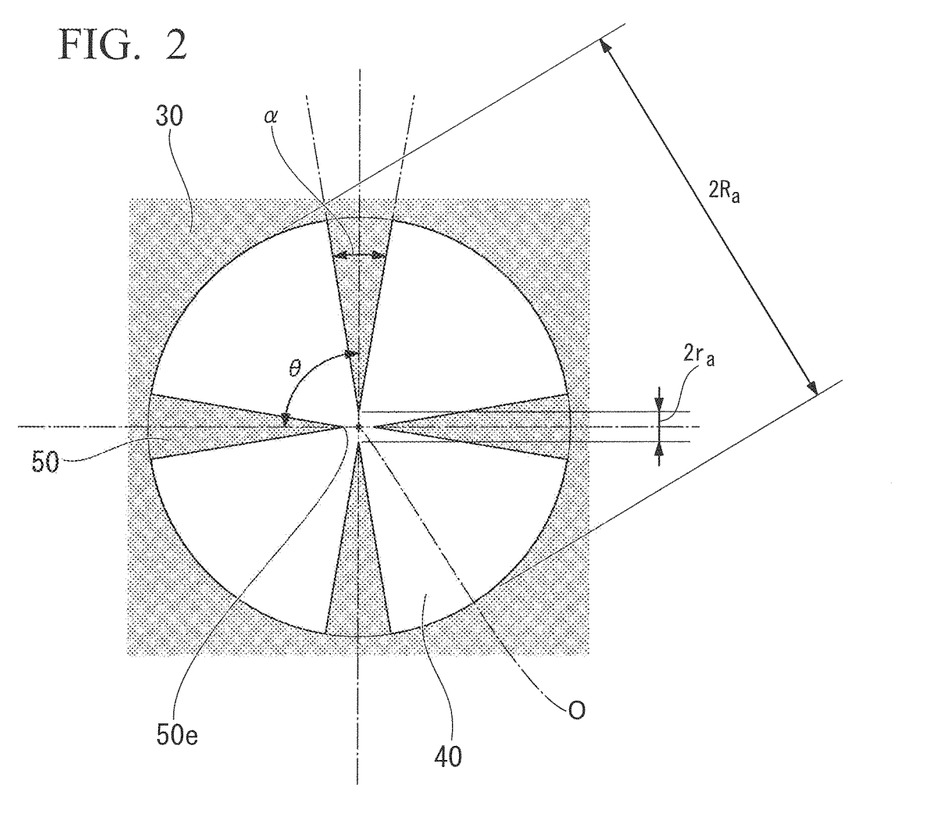
FIG. 2 is a schematic diagram of an aperture pattern (when the number of tips $N_t$ is 4) according to an embodiment of the present invention.
Figure 2A:
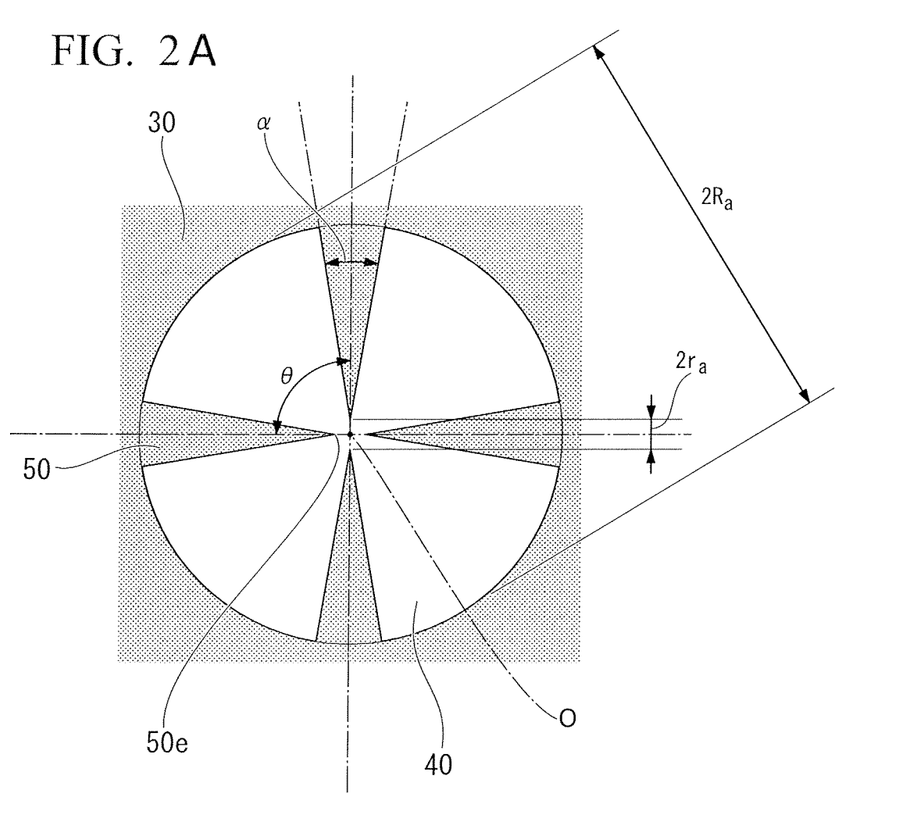
FIG. 2A is a schematic diagram of an aperture pattern (when the number of tips $N_t$ is 4) according to an embodiment of the present invention.
Figure 2B:
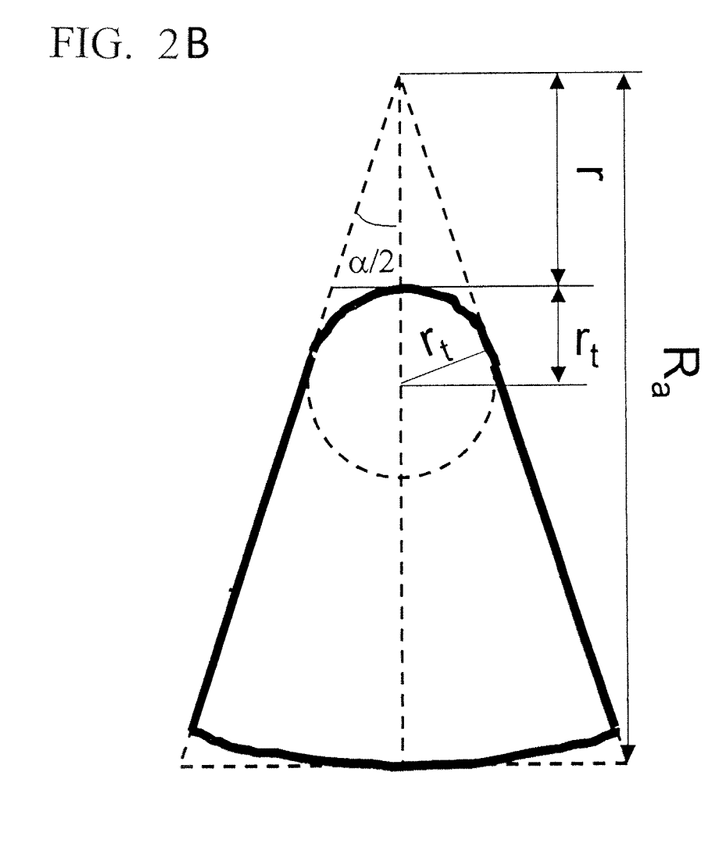
FIG. 2B is a schematic representation of one of the tips shown in FIG. 2.

As shown in FIG. 2, a plurality of tips 50 that are tapered toward the center from the edge (outer periphery of the circular region) are provided in the circular region. It is preferable that the number of tips 50 be 4 to 320. An odd number of tips 50 may be provided, or an even number of tips 50 may be provided. It is preferable that the tip flare angle α of a tip apex 50e of the tip 50 be 1.15 to 40°. In addition, it is preferable that the shortest distance between the tip apexes disposed opposite each other be 0.1 to 10 μm.

The tip 50 may have a fan shape surrounded by an arc having a radius of curvature, which is the same as the radius of the circular region, and two straight sides extending from both ends of the arc. In this case, the tip flare angle α of the tip apex 50e is substantially equal to the angle formed by the two sides. In the fan-shaped tip 50, the lengths of the two sides may be substantially equal.

FIG. 2 shows an example of the aperture region formed in the mask 30, and a gray portion is the mask 30 formed of the material 2 and a white portion is the aperture 40. The tip 50 is formed of the same conductive material 2 as the mask 30. A portion, which is not covered by the tip 50, in the circular region forms the aperture 40. All of the tips 50 have the same shape, and all angles between adjacent tips (θ in FIG. 2) are equal and are expressed as 360°/$N_t$. $N_t$ means the number of tips. Here, the angle between adjacent tips is an angle formed by the lines drawn from the tip apexes of the adjacent tips to the center of the circular region, in other words, the angle between adjacent tips is an angle formed by the lines drawn from the centers of the arcs of the adjacent tips to the center of the circular region.

The spot size of a transmitted wave decreases as the diameter ($2R_a$ in FIG. 2) of the circular region where the aperture 40 is formed decreases. The diameter of the circular region is set to be less than or equal to ⅕ of the wavelength λ of the incident wave. For example, for the incident wave (wavelength λ=300 μm) with a frequency of 1 THz, the aperture diameter $2R_a$ is set to be less than or equal to 60 μm. Since the wavelength of the terahertz wave is in a range of 0.03 to 3 mm, it is preferable that the range of $R_a$ be set to 0.003 mm≤$R_a$≤0.3 mm.

Although the circular region where the aperture 40 is formed is located in the center of the mask 30 in the embodiment shown in FIG. 1, the position at which the aperture 40 is formed may be selected according to the shape or application of an optical element.

If the tip flare angle α of the tip 50 is larger than 40°, the transmittance of 2.5% or more cannot be realized because the electromagnetic field enhancing effect at the tip apex 50e of the tip is reduced. For this reason, it is preferable that the tip flare angle α be set to be less than or equal to 40°.

It is preferable that the shortest distance $2r_a$ between the tip apexes of the tips 50 (tip apexes of the opposite tips 50) satisfy the relationship of $r_t ≤ r_a ≤ 5r_t$ assuming that $r_t$ is the radius of curvature of the tip apex of the tip, in terms of maximizing the interference of the electromagnetic field generated at the tip apexes of tips and increasing the intensity of a transmitted wave.

In addition, it is preferable that the number $N_t$ of the tips 50 satisfy 4≤$N_t$≤360°/α assuming that the tip flare angle α is defined as α=2 arc sin [$r_t/(r_t+r_a)$]. On the other hand, from the spot size of the available beam as focused ion beams or the like, the value of $N_t$ is limited to the extent of up to 320 since α≅0.02 (rad)≅1.15° assuming that $r_t$ and $r_a$ as FIB processing accuracy are $r_t$=50 nm and $r_a$=5000 nm.

Figure 3:
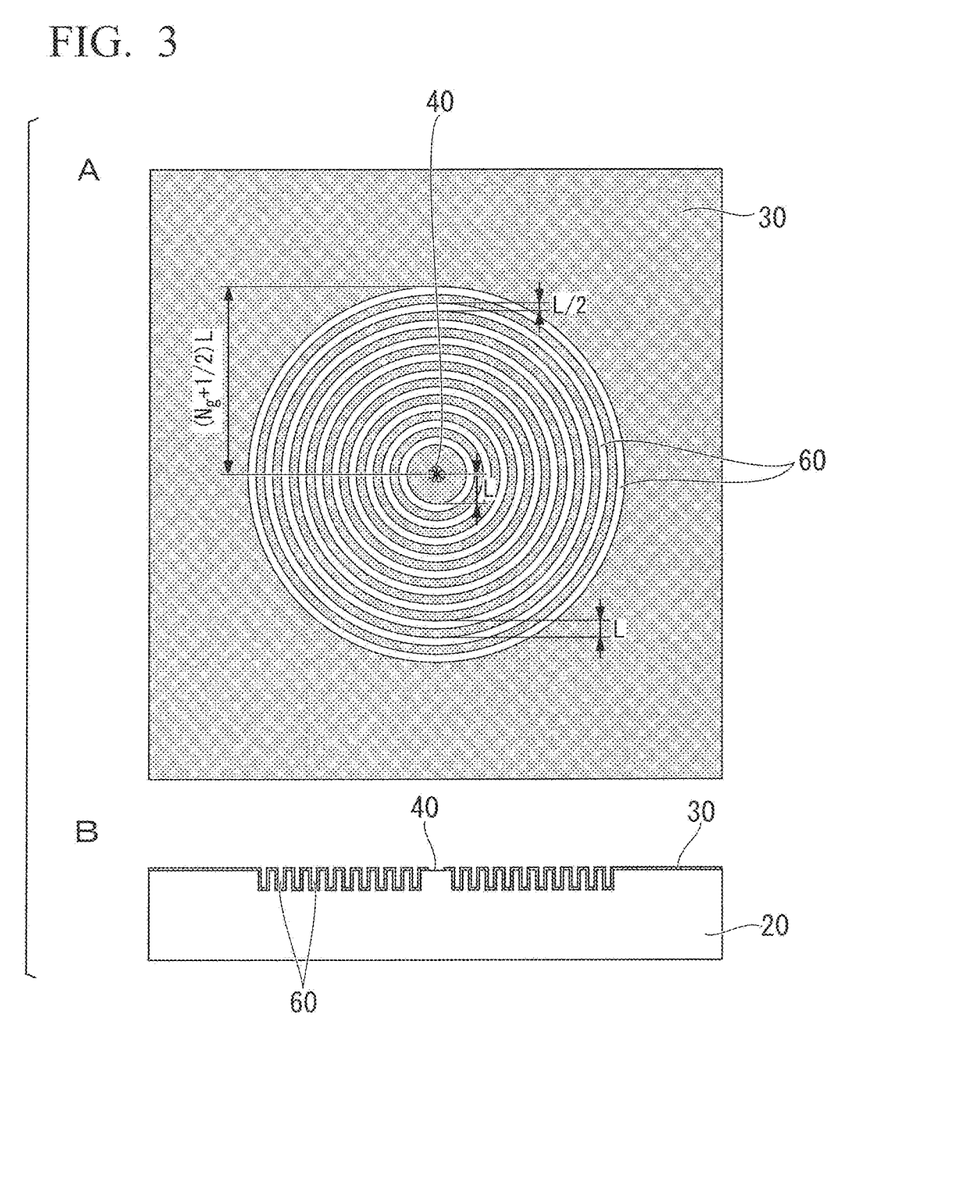
FIG. 3(A) is a plan view of the optical element according to an embodiment of the present invention when viewed from the mask surface side (B surface in FIG. 1)
FIG. 3(B) is a cross-sectional view of a plane passing through an aperture of the optical element according to the embodiment of the present invention showing the shape thereof.

An upper diagram A of FIG. 3 is a plan view when the optical element is viewed from the mask surface side, and a lower diagram B is a cross-sectional view of a cross section passing through the aperture 40.

As shown in the cross-sectional view B of FIG. 3, a ring-shaped groove 60 is configured by forming a ring-shaped groove on a substrate (substrate 20) surface and then forming the mask 30 on the substrate surface.

As shown in the plan view A of FIG. 3, it is preferable to form four or more rin g-shaped grooves that are formed so as to have the same center as the aperture and surround the aperture. The width L/2 of each ring is equally fixed, and its radius is increased by an equal amount L from the innermost side. In this case, it is preferable that the inner radius of the innermost ring be L since the surface wave interference is largest at the aperture. That is, assuming that the inner radius of the innermost ring-shaped groove is L, it is preferable that the width of each groove be L/2 and the difference between the inner radii of adjacent grooves be L.

It is preferable that the ring-shaped groove 60 be formed in the entire region (spot region) irradiated with incident electromagnetic waves. Assuming that the spot shape of an incident wave is a circle and its radius is $R_i$, it is preferable that the number $N_g$ of ring-shaped grooves 60 be greater than or equal to $(2R_i-L)/2L$.

In addition, it is preferable that the thickness of the substrate 20 be 0.1 to 3.0 mm. If the thickness is less than or equal to 0.1 mm, the influence of not only the diffraction peak due to the aperture 40 but also multiple reflection within the substrate is increased. On the contrary, if the thickness is greater than or equal to 3.0 mm, transmission intensity within the substrate is reduced, in addition, the substrate 20 is a parallel plate, and its size needs to be larger than the outer radius $(N_g+\frac{1}{2})L$ of the maximum ring-shaped groove as shown in FIG. 3.

In the optical element 100 of the present invention, it is preferable that the substrate 20 be formed of any of Si, crystal, sapphire, terahertz wave transmissive resin (polyethylene, polypropylene, TEFLON® (polytetrafluoroethylene (PTFE) based formulas), polymethyl menthene, and the like) and terahertz wave transmissive glass.

In the optical element 100 of the present invention, it is preferable that the thickness of the mask 30 be 0.1 to 1.0 μm. If the thickness is less than 0.1 μm, it is smaller than the skin depth of the electromagnetic wave. Accordingly, since the terahertz wave can be even transmitted through a non-aperture portion of the mask 30, the enhancing effect at the tip apex 50e of the tip does not work. On the other hand, the transmittance is maintained at the maximum level if the thickness exceeds 1.0 μm, and decreases as the thickness increases further. For this reason, it is preferable that the thickness of the mask 30 be 0.1 to 1.0 μm. The element 100 of the present invention can increase the propagation distance of surface electromagnetic waves as the electrical conductivity of the mask 30 increases. Accordingly, it is possible to increase the resonance peak due to the ring-shaped groove 60 and also to increase the current density of the tip 50 in the aperture. As a result, the intensity of the transmitted electromagnetic wave is increased. For this reason, it is preferable that the mask 30 be formed of metal or alloy. In the element of the present invention, it is preferable that the metal be any metal of Al, Au, Cu, Ag, Pt, Cr, and Ni or an alloy thereof.

By irradiation of terahertz waves, electromagnetic surface waves propagate through the mask surface (B surface). In this case, since ring-shaped grooves are periodically present on the mask surface, the resonance of surface waves occurs corresponding to the periodic distance between the ring-shaped grooves 60, resulting in a state where the strength of the electromagnetic field changes depending on the position of the unevenness of the ring-shaped groove (regarding this phenomenon, refer to NPL 2 and NPL 5). When the radius of the innermost ring-shaped groove is set to the above-described L by adjusting the width and the inner radius of each groove as described above, the maximum resonance peak can be obtained at the aperture position. L needs to be larger than $R_a$ that is an aperture diameter.

The electromagnetic field of the aperture is maximized due to surface wave resonance by the ring-shaped groove 60. In addition, at the tip apex 50e of the tip in the aperture region, the acuter the angle of the tip 50 is, the more the cross-sectional area is reduced. Accordingly, since the current density increases from the edge of the tip 50 toward the tip apex, a very high electromagnetic field is formed in the very vicinity of the tip apex 50e of the tip. If the tip apexes 50e of the plurality of tips 50 are present in the neighborhood, electromagnetic fields around the tip apexes interfere with each other. As a result, the electromagnetic field is further enhanced. This enhanced electromagnetic field vibrates corresponding to the frequency of the terahertz wave incident on the mask surface, and an electromagnetic wave is emitted from the back surface (B surface in FIG. 1) of the mask due to the vibration of the electromagnetic field. This is detected as a transmitted wave that has been transmitted through the entire optical element.

Assuming that the distance between the ring-shaped grooves 60 is L, it has been found out that the wavelength λ of the electromagnetic wave that gives the maximum resonance peak of the surface wave is $\lambda=n_{eff}L$ (refer NPL 2). $n_{eff}$ is defined as an effective refractive index, and is expressed as $n_{eff}=[\epsilon_s \epsilon_m/(\epsilon_s+\epsilon_m)]^{1/2}$. Here, $\epsilon_m$ is a real part of the dielectric constant of a mask, and $\epsilon_s$ is a real part of the dielectric constant of a substrate. The absolute value of $\epsilon_m$ of the metal mask is much larger than that $\epsilon_s$ of the substrate. After all, the effective refractive index $n_{eff}$ can be rewritten as $n_{eff} \cong [\epsilon_s]^{1/2} \cong n_s$ using the refractive index $n_s$ of the substrate. Accordingly, the distance L between the ring-shaped grooves 60 required to cause resonance on the mask surface can be rewritten as $L=\lambda/n_s$. By setting the resonance wavelength λ and the dielectric constant $n_s$ of the substrate in advance from this expression, it is possible to determine the width L of the ring-shaped groove 60 required to cause the resonance. Accordingly, L needs to be larger than $R_a$ that is a diameter of a central aperture region. In addition, in order to have a resonance frequency in the wavelength range (30 to 3000 μm) of a terahertz wave, L needs to be in the range of $R_a<L<3$ mm.

FIRST EXAMPLE

A fine aperture manufacturing method and the performance of an optical element manufactured as an example will be described.

As a process, a mask was formed on a substrate in the following manner using a lithography method.

Figure 4:
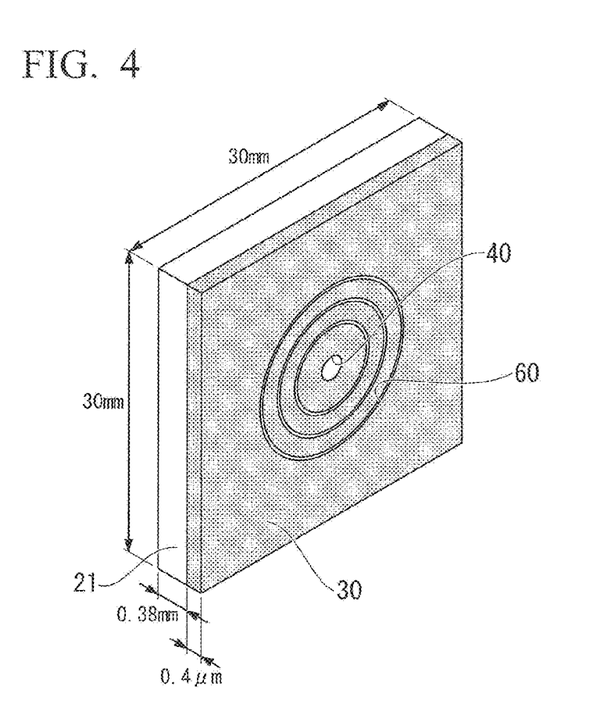
FIG. 4 is a diagram showing the shape of an entire optical element of a first example and the arrangement thereof with respect to an incident wave.

First, as shown in FIG. 4, a high-resistance single-crystal Si substrate 21 whose both surfaces were mirror-polished and which had a plate thickness of 380 μm and a size of 30 mm (vertical)×30 mm (horizontal) was prepared, and the ring-shaped groove 60 was manufactured first as follows. An Ni layer having a thickness of 0.25 μm was formed on one surface of the Si substrate 21 by sputtering. A 1,1,1,3,3,3-hexaethyldisilazane layer was formed on the Ni layer by spin coating, and then a photoresist (OFPR800LB manufactured by Tokyo Ohka Kogyo Co., Ltd.) layer was formed on the 1,1,1,3,3,3-hexamethyldisilazane layer by spin coating and heating on the hot plate was performed at 90° C. for 180 seconds. After placing an exposure mask with a predetermined pattern on the photoresist, ultraviolet exposure was performed with the intensity of 18 mW/cm³ for 10 seconds. Then, development using a developer (NMD3 (2.38 wt % aqueous solution of tetramethyl ammonium hydroxide) manufactured by Tokyo Ohka Kogyo Co., Ltd.) was performed, and heating on the hot plate was performed again at 120° C. for 120 seconds.

Figure 5:
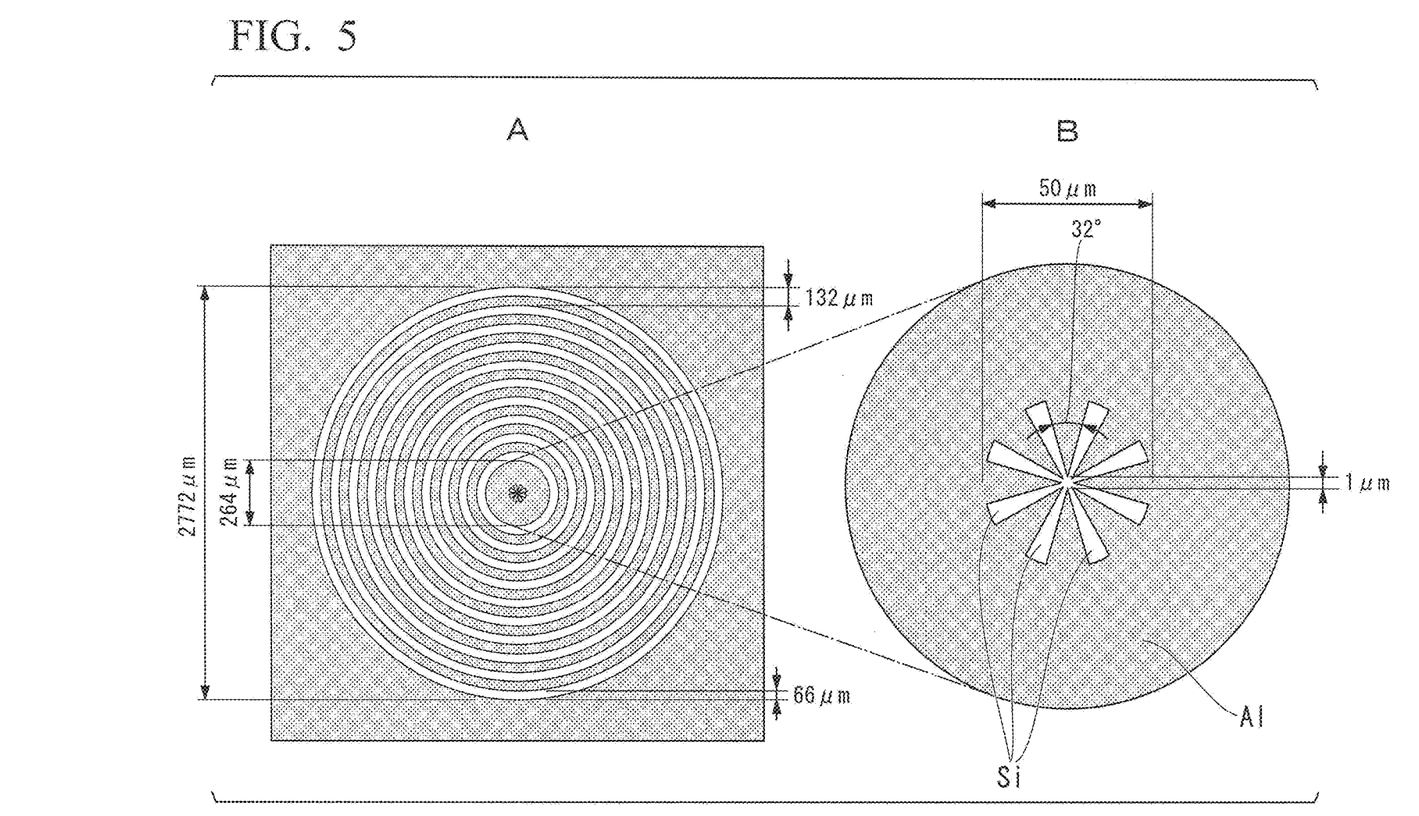
FIG. 5A is a diagram of all ring-shaped grooves (left) and FIG. 5B is an enlarged view of the aperture (right) when viewed from the mask surface side of the optical element of the first example.

Then, Ni was etched using an aqueous solution of ammonium persulfate and then the photoresist was removed by stripping solution, thereby drawing an Ni mask on the Si substrate. By plasma-etching this for 5500 seconds, a pattern was formed on the Si substrate. Then, ten ring-shaped grooves were formed as shown in FIG. 5 by removing the entire Ni layer using the aqueous solution of ammonium persulfate.

Figure 6:
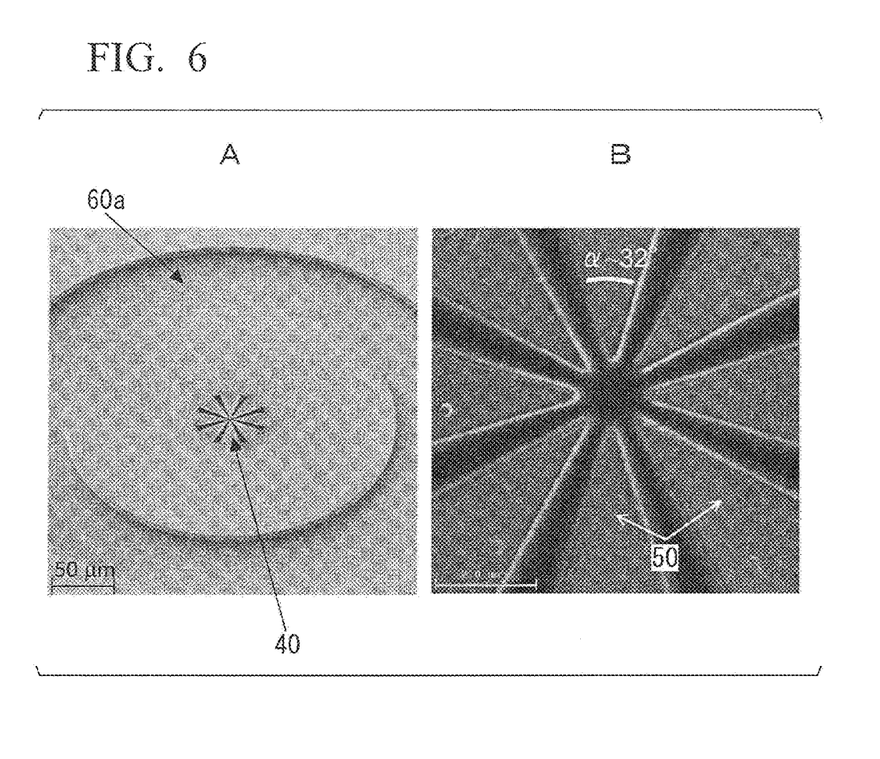
FIGS. 6A and 6B are an electron microscope photographs of a mask aperture of the manufactured optical element.
Figure 7:
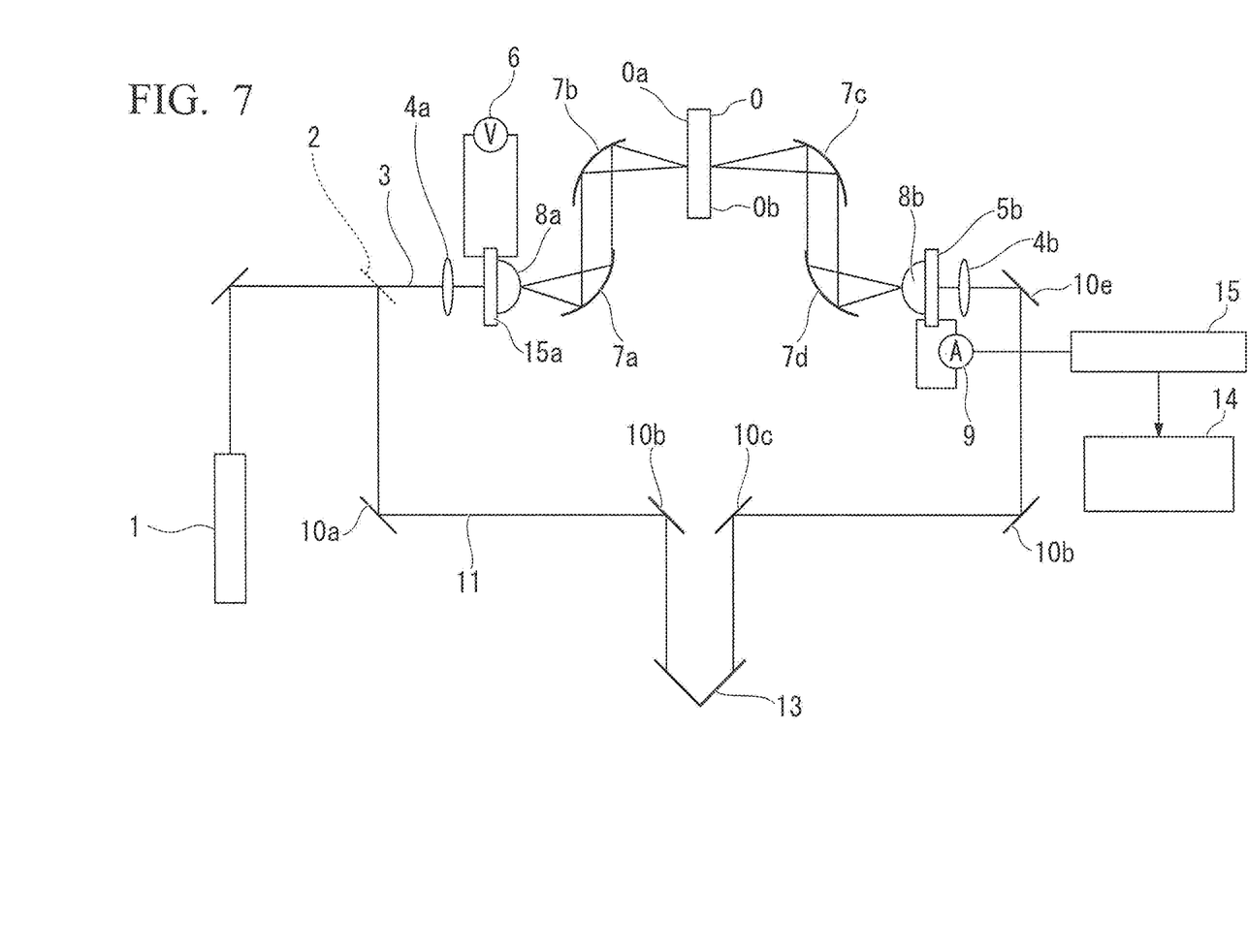
FIG. 7 is a schematic diagram of an optical system used to evaluate the terahertz wave transmittance of the optical element.
Figure 8:
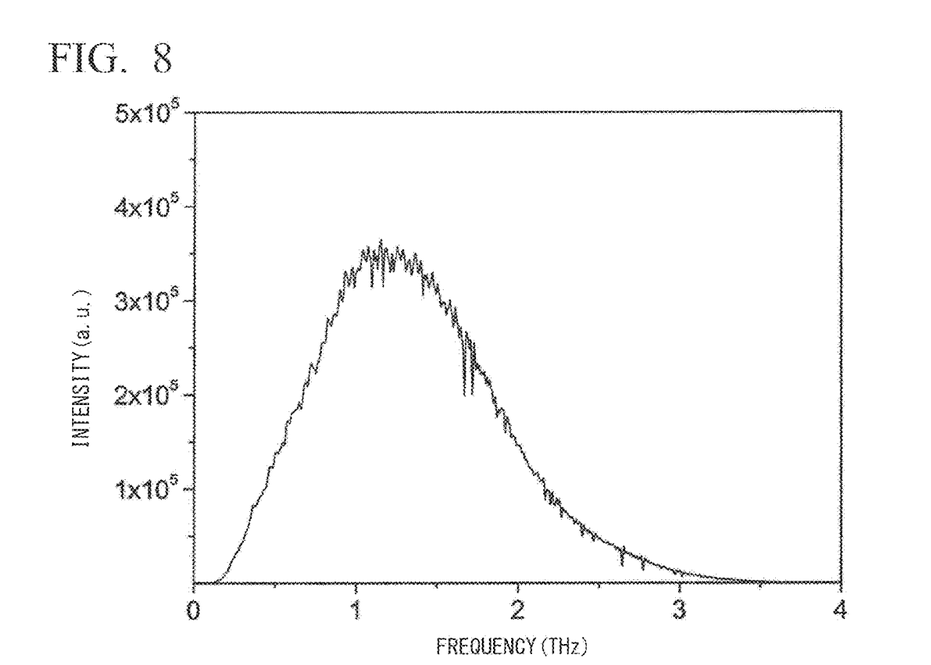
FIG. 8 shows a frequency characteristic of an incident wave used in measurement of the transmittance.

Finally, an aluminum layer with a thickness of 0.4 μm was formed on the Si substrate after the groove processing by sputtering. This was a mask 31 having the ring-shaped groove 60. In addition, for the aperture 40, an aperture shape shown in the photographs in FIG. 6 was obtained by removing the A1 portion with focused ion beams such that the design shown in the right figure of FIG. 5 was obtained. That is, eight tips having an tip flare angle of 32° were formed in a circular region 50 having a diameter of 50 μm. The distance between the tip apexes of the opposite tips was 1 μm. A white portion which is not covered by tips is an aperture, and Si is exposed through the aperture. The left A of FIG. 6 is a photograph of the aperture 40 and the innermost ring-shaped groove 60a, and the right B of FIG. 6 is an enlarged photograph of the aperture 40. In FIG. 6, a black portion between tips is a portion where Al is removed and the Si substrate is exposed, The transmittance of the terahertz wave transmitted through the optical element manufactured as an example of the present invention was measured using a terahertz time-domain spectroscopy apparatus (IRS-2000 manufactured by Advanced infrared Spectroscopy Co., Ltd.) shown in FIG. 7. In the apparatus shown in FIG. 7, 0 indicates a band pass filter having two surfaces 0a and 0b. 1 indicates a femtosecond pulse laser. 2 indicates a beam splitter. 3 indicates pump light. 4a and 4b indicate lenses. 5a and 5b indicate photoconductive antennas. 6 indicates a voltmeter. 7 indicates an off-axis parabolic mirror. 8a and 8b indicate silicon lenses. 9 indicates an ammeter. 10a, 10b, 10c, 10d and 10e indicate mirrors. 11 indicates probe light. 13 indicates a corner reflector. 14 indicates a recording system. 15 indicates a current amplifier. In this apparatus, a sample was placed at the position of the band pass filter indicated by the reference numeral 0 in FIG. 7 and electromagnetic waves transmitted through the sample were measured. FIG. 8 shows a frequency characteristic of an incident wave measured by performing measurement without placing a sample in the evaluation apparatus of FIG. 7, and it can be seen that the band of the incident terahertz wave in this evaluation apparatus is 0.2 to 3.5 THz.

Figure 9:
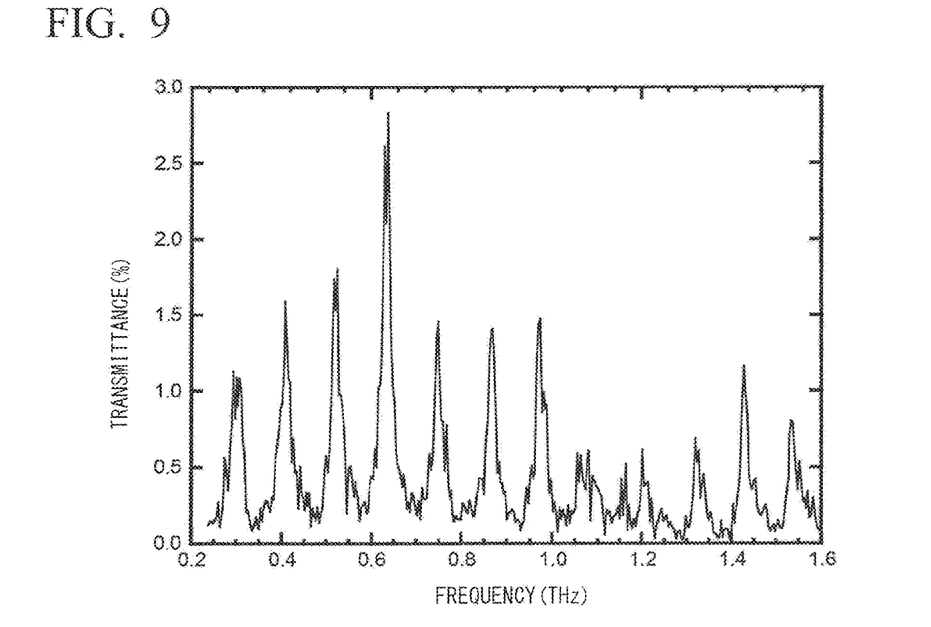
FIG. 9 shows a change in transmittance with respect to the frequency of the terahertz wave transmitted through the optical element.

This band is 85.4 to 1500 μm when converted into wavelength. For this reason, the aperture diameter 50 μm of the invented element is sufficiently smaller than the wavelength of the incident terahertz wave. FIG. 9 shows a change in the transmittance versus frequency for a detection wave transmitted through the optical element. A periodic peak occurs due to multiple reflection within the silicon substrate, and the maximum transmittance is about 2.8% at the frequency of 0.64 THz (470 μm converted into wavelength). It has been described above that the maximum resonance peak wavelength is expressed as $\lambda = n_{eff} L$. When the distance L between ring-shaped grooves in the manufactured optical element is 132 μm and the literature value 3.417 is used as a value of the refractive index $n_{si}$ of high-resistance single-crystal silicon, an expected resonance peak wavelength is 451 μm. This indicates that the expected resonance peak wavelength satisfactorily matches the actual value of 470 μm shown in FIG. 9. Presumably, the slight difference is due to the difference in the refractive index of the actually used silicon substrate.

The radius of a circle having the same size as the area of a portion (white region in the circle in FIG. 2), through which an electromagnetic wave can actually pass, of the generated aperture 40 is defined as an effective aperture radius $r_{effective}$. In the case of a circular aperture having the same area as this $r_{effective}$, the transmittance can be theoretically calculated. The ratio between this transmittance and the transmittance of the optical element in this example can be written as in expression 1 (NPL 4).

$$\frac{T_{example}}{T_{circle}} \approx \frac{0.03 \cdot 243}{2048[R_a^2 - \alpha(R_a^2 - r_a^2)/45°]} \frac{\lambda^6}{r_{effective}^4} \quad \text{(Expression 1)}$$

Here, $T_{example}$ is the transmittance in this example, $T_{circle}$ is the transmittance in the case of a circular aperture, $R_a$ is the radius of the circular region where the aperture is formed (refer to FIG. 2), $r_a$ is the radius of the central cavity surrounded by the tip apexes of the tips (refer to FIG. 2), $\alpha$ is the tip flare angle of the tip apex of the tip (refer to FIG. 2), and $\lambda$ is a wavelength (470 μm) at 0.64 THz showing the maximum transmittance. As a result, it became apparent that the optical element of the present invention had a transmittance of $10^6$ times the transmittance in the case of a simple circular aperture.

Figure 10:
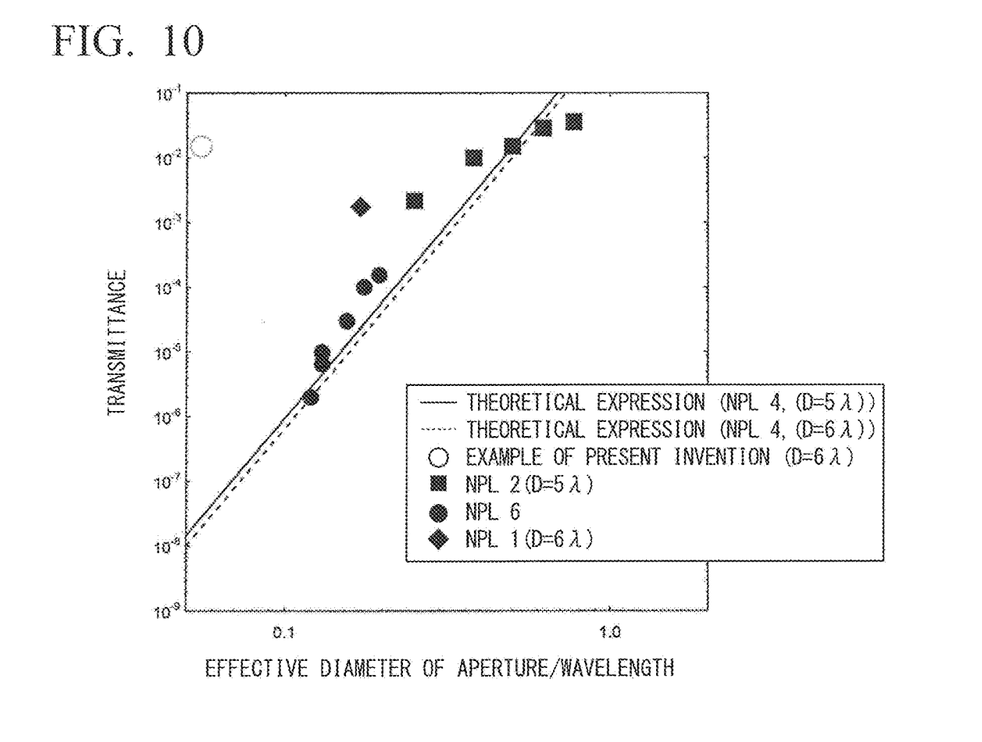
FIG. 10 is a diagram showing a comparison between the results of the example of the present invention and the results reported in prior art, in which the horizontal axis indicates a ratio of the effective diameter of the aperture to the wavelength and the vertical axis indicates a transmittance. A white circle indicates the example of the present invention, a black diamond indicates a numeric value according to NPL 1, a black rectangle indicates a numeric value according to NPL 2, and a black circle indicates a numeric value according to NPL 6. The solid line and the dotted line indicate the numeric value of theoretical expression in NPL 4, and the solid line indicates a case of D=5λ and the dotted line indicates a case of D=6λ.
Figure 11:
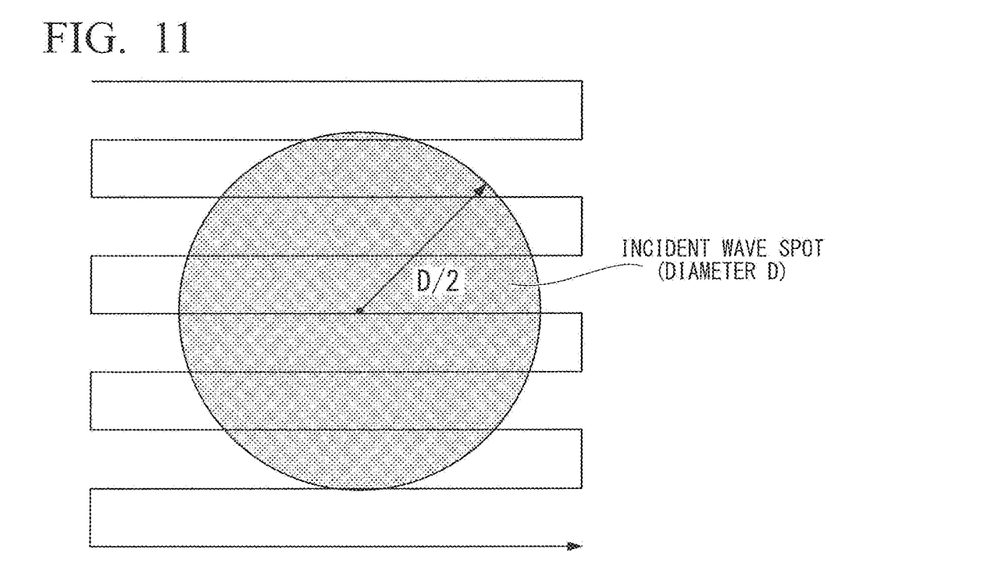
FIG. 11 is a schematic diagram illustrating a measurement method for scanning an optical element within the plane perpendicular to an incident electromagnetic wave and visualizing the electric field in the space. The circular region indicates the spot of an incident wave. The solid line drawn from the upper left to the lower right while moving left and right indicates the scan trajectory of the optical element.

FIG. 10 shows the comparison between the estimates based on the theoretical expression and the data reported in known literatures (NPL 1, NPL 2, NPL 4, and NPL 6) up to now and a result of the transmittance in this example. The horizontal axis is a logarithmic scale, and indicates a value obtained by dividing twice the effective radius of the aperture, that is, the effective diameter by the wavelength of an electromagnetic wave. The transmittance of an electromagnetic wave depends on the wavelength of an incident wave and the diameter D of an incident beam. For this reason, since D=6λ is satisfied in this example, results for the comparable incident beam diameters are plotted. In NPL 6, this is not known since the beam diameter information is not disclosed. In addition, since the theoretical expression for the circular aperture has been proposed in NPL 4, the analysis results for D=6λ and D=5λ are shown by the solid line and the dotted line, respectively, in the present invention, the transmittance was 2.8% at the effective diameter 26 μm of the aperture and the wavelength 470 μm indicating the maximum transmittance. From this result, it can be seen, that a very high transmittance is achieved with the much smaller aperture area compared with the trend expected from the conventional reported cases or theories.

Figure 12:
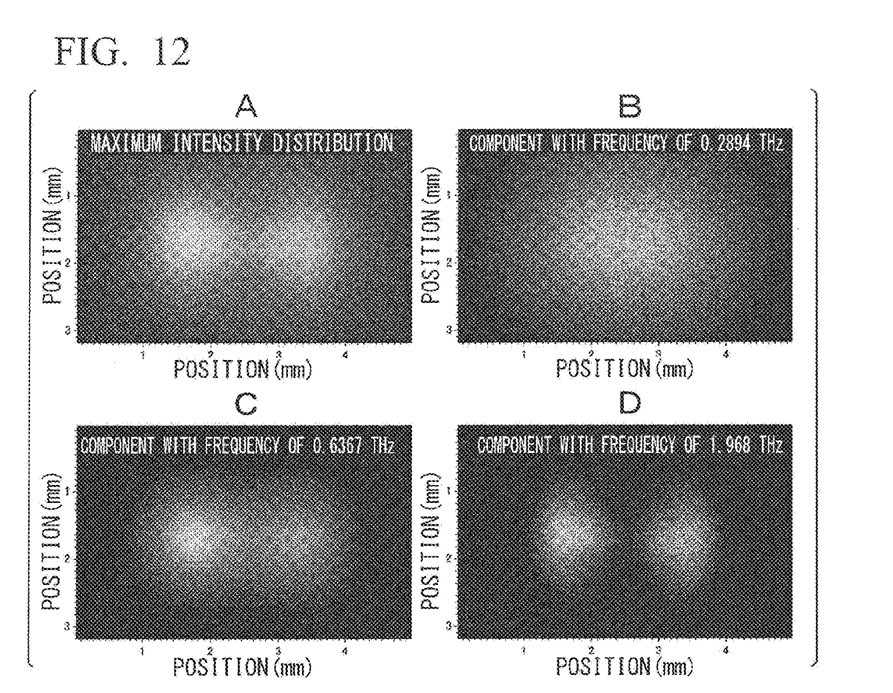
FIGS. 12A, 12B, 12C and 12D are transmission intensity distribution diagrams of incident electromagnetic waves visualized by the method of FIG. 11 using an optical element, and shows an electric field distribution on the space in a scan cross-section obtained by moving the element every 20 μm within the plane perpendicular to the incident electromagnetic waves and detecting the electromagnetic waves transmitted through the element at each point. Accordingly, the minimum pixel size of this image is 20×20 μm$^2$. A is a maximum intensity distribution diagram of the transmitted wave at each point, B is an intensity distribution diagram of a component with a frequency of 0.2894 THz at each point, C is an intensity distribution diagram of a component with a frequency of 0.6367 THz at each point, and D is an intensity distribution diagram of a component with a frequency of 1.968 T-Hz at each point.

In addition, as shown in FIG. 1, the invented optical element was scanned in a two-dimensional manner every 20 μm within the plane perpendicular to the incident direction of an incident beam. Although the spot diameter D was about 2800 μm, a very clear cross-sectional profile of the electromagnetic wave propagating through space as shown in FIG. 12 was able to be obtained by using this element. By using this optical element, it was possible to obtain an image with high resolution exceeding the limit by the wavelength (several hundred micrometers to several millimeters) of the terahertz electromagnetic wave.

Figure 13:
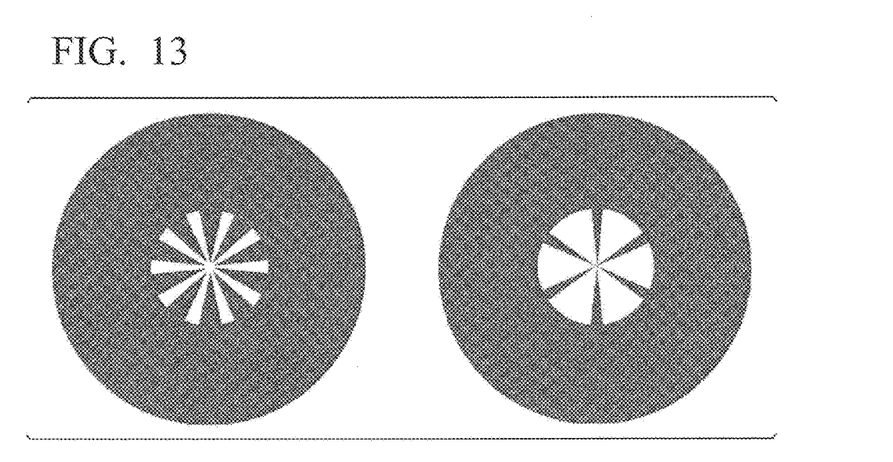
FIG. 13 is a schematic diagram showing an example of the aperture shape.

In addition, the present invention is not limited by the above-described example. For example, FIG. 13 illustrates two examples for the aperture structure considered. The left is an example when the number of tips is 10, and the right is an example when the number of tips is 6.

INDUSTRIAL APPLICABILITY

If the optical element of the present invention is used, it is possible to manufacture a high-resolution terahertz microscope. As a result, it is possible to invent an analyzer for analyzing the molecular structure of a polymer material or a DNA structure analyzer. In addition, it is possible to invent a medical fluoroscopy apparatus, which does not have an adverse effect on the human body, like conventional X-rays, or semiconductor chip fluoroscopy equipment.

The invention claimed is:

1. An optical element for terahertz waves that transmits terahertz-wave incident beams through itself after being compressed into half or less a wavelength of the terahertz-wave incident beam, the optical element comprising:
   a substrate that allows terahertz waves to be transmitted through itself; and
   a conductive coat that covers a single surface of the substrate and is capable of blocking the terahertz waves,
   wherein the coat has an aperture having a center provided in a circular region, and
   wherein a plurality of concentric ring-shaped grooves are formed in both the conductive coat and the substrate, the plurality of concentric ring-shaped grooves having the same center as the circular region and having radii that successively increase by a fixed length, and
   wherein the plurality of concentric ring-shaped grooves comprises an innermost groove having an inner radius equal to the fixed length, and
   wherein four or more fan-shaped tips are formed in the circular region, each tip having an arc with the same radius of curvature as a radius of the circular region, the four or more fan-shaped tips being arranged at equal distances circumferentially around the center of the circular region, each tip having an apex pointing toward the center of the circular region circle without being in contact with each other in a state where the arc is in contact with an outer periphery of the circular region, and
   wherein the tips have an apex radius, $r_t$, an opposite tip apex separation distance, $2r_a$, a tip flare angle, $\alpha$, and there are an even number of the tips, $N_t$, and wherein the tips are arranged with the following restrictions:

$$1 < r_t < 200\text{nm}, r_t < r_a < 5r_t, \text{ and } 4 < N_t < 360°/\alpha, \text{ where}$$
$$\alpha = 2\arcsin\lfloor r_t/(r_t + r_a) \rfloor.$$

2. The optical element according to claim 1, wherein a shortest distance between tip apexes of the tips is 0.1 to 10 µm.

3. The optical element according to claim 1, wherein, assuming that a tip flare angle of a tip apex of each tip is $\alpha$, $1.15° \leq \alpha \leq 40°$.

4. The optical element according to claim 1, wherein the number of tips present in the circular region is 4 to 320.

5. The optical element according to claim 1, wherein, assuming that the radius of the circular region is $R_a$, $0.003$ mm $\leq R_a \leq 0.3$ mm.

6. The optical element according to claim 1, wherein the circular region is located in the center of the coat.

7. The optical element according to claim 1, wherein the coat is formed of any metal of Al, Au, Cu, Ag, Pt, Cr, and Ni or an alloy of the metals.

8. The optical element according to claim 1, wherein the substrate is formed of any material selected from the group consisting of silicon, crystal, sapphire, polyethylene, polypropylene and polytetrafluoroethylene (PTFE) based formulas.

* * * * *